US012226660B2

(12) United States Patent
Vignot et al.

(10) Patent No.: US 12,226,660 B2
(45) Date of Patent: Feb. 18, 2025

(54) IMPLANTABLE MEDICAL DEVICE FOR IMAGING AND/OR TREATMENT OF BRAIN TISSUE

(71) Applicant: CARTHERA, Lyons (FR)

(72) Inventors: Alexandre Vignot, Lyons (FR); Matthieu Cholvy, Peage de Roussillon (FR)

(73) Assignee: CARTHERA, Lyons (FR)

( * ) Notice: Subject to any disclaimer, the term of this patent is extended or adjusted under 35 U.S.C. 154(b) by 242 days.

(21) Appl. No.: 17/777,650

(22) PCT Filed: Nov. 25, 2020

(86) PCT No.: PCT/EP2020/083313
§ 371 (c)(1),
(2) Date: May 18, 2022

(87) PCT Pub. No.: WO2021/105179
PCT Pub. Date: Jun. 3, 2021

(65) Prior Publication Data
US 2023/0029295 A1 Jan. 26, 2023

(30) Foreign Application Priority Data

Nov. 25, 2019 (FR) ...................................... 1913189

(51) Int. Cl.
A61N 7/00 (2006.01)
A61B 8/08 (2006.01)
(52) U.S. Cl.
CPC .............. A61N 7/00 (2013.01); A61B 8/0808 (2013.01); A61N 2007/0021 (2013.01);
(Continued)

(58) Field of Classification Search
CPC ....... A61B 8/42; A61B 8/4272; A61B 8/0808; A61N 7/00; A61N 2007/0004;
(Continued)

(56) References Cited

U.S. PATENT DOCUMENTS 5,230,338 A 7/1993 Allen et al.
5,524,624 A * 6/1996 Tepper ..................... A61N 7/00
607/51
(Continued)

FOREIGN PATENT DOCUMENTS

CH 711264 A2 12/2016
EP 1047362 A1 11/2000
(Continued)

OTHER PUBLICATIONS

English abstract provided for foreign reference FR 3078879 A1.
English abstract provided for foreign reference CH 711264 A2.

Primary Examiner — Carolyn A Pehlke
(74) Attorney, Agent, or Firm — BCF LLP

(57) ABSTRACT

The present invention relates to an implantable device (1) comprising: —an ultrasonic unit (11) which includes an electric connection terminal, —a support plate (12) which includes a through-opening for the connection terminal to pass through, and —an attachment piece (13) which can cooperate with the connection terminal, the attachment piece (13) including a collar for pressing the support plate (12) against the ultrasonic unit (11) when the ultrasonic unit (11), the support plate (12) and the attachment piece (13) are joined.

11 Claims, 4 Drawing Sheets

(52) U.S. Cl.
CPC ............... *A61N 2007/0043* (2013.01); *A61N 2007/0052* (2013.01); *A61N 2007/0078* (2013.01)

(58) Field of Classification Search
CPC .... A61N 2007/0021; A61N 2007/0026; A61N 2007/003
See application file for complete search history.

(56) References Cited

U.S. PATENT DOCUMENTS

| | | | |
|---|---|---|---|
| 6,932,842 | B1 | 8/2005 | Litschko et al. |
| 7,479,146 | B2 | 1/2009 | Malinowski |
| 7,651,506 | B2 | 1/2010 | Bova et al. |
| 8,936,601 | B2 | 1/2015 | Carignan et al. |
| 8,974,535 | B2 | 3/2015 | Antonyshyn et al. |
| 9,044,195 | B2 | 6/2015 | Manwaring et al. |
| 9,504,402 | B2 | 11/2016 | Wahlstrand |
| 9,744,042 | B2 | 8/2017 | Beerens et al. |
| 2002/0052610 | A1 | 5/2002 | Skakoon et al. |
| 2004/0102778 | A1 | 5/2004 | Huebner et al. |
| 2004/0267234 | A1* | 12/2004 | Heart .............. A61M 31/002 604/500 |
| 2007/0129652 | A1 | 6/2007 | Nita |
| 2007/0225773 | A1 | 9/2007 | Shen et al. |
| 2008/0004676 | A1 | 1/2008 | Osypka et al. |
| 2009/0112278 | A1 | 4/2009 | Wingeier et al. |
| 2009/0112280 | A1 | 4/2009 | Wingeier et al. |
| 2012/0078140 | A1 | 3/2012 | Nita |
| 2012/0179147 | A1 | 7/2012 | Geebelen et al. |
| 2013/0204316 | A1* | 8/2013 | Carpentier .............. A61B 8/56 607/45 |
| 2013/0345599 | A1 | 12/2013 | Lin et al. |
| 2014/0277019 | A1 | 9/2014 | Pearson |
| 2015/0196369 | A1 | 7/2015 | Glossop |
| 2015/0265448 | A1 | 9/2015 | Haberl et al. |
| 2017/0172585 | A1 | 6/2017 | Pfeiffer et al. |
| 2017/0273794 | A1 | 9/2017 | Howard et al. |

FOREIGN PATENT DOCUMENTS

| | | |
|---|---|---|
| EP | 2515750 A2 | 10/2012 |
| EP | 2539021 A2 | 1/2013 |
| EP | 3233187 A2 | 10/2017 |
| FR | 3078879 A1 | 9/2019 |
| WO | 2009115283 A1 | 9/2009 |
| WO | 2009132389 A1 | 11/2009 |
| WO | 2011101039 A1 | 8/2011 |
| WO | 2017001911 A1 | 1/2017 |

* cited by examiner

IMPLANTABLE MEDICAL DEVICE FOR IMAGING AND/OR TREATMENT OF BRAIN TISSUE

CROSS-REFERENCE TO RELATED APPLICATIONS

This application is a national phase filing under 35 U.S.C. § 371 of International Application No. PCT/EP2020/083313 filed on Nov. 25, 2020, which claims benefit of priority from French Patent Application No. 1913189 filed Nov. 25, 2019, the contents of each of which are hereby incorporated by reference in their entirety.

FIELD OF THE INVENTION

The present invention relates to the general technical field of ultrasonic devices for the treatment of human or animal brain tissue by ultrasound in order to help a practitioner in the treatment of a pathology.

BACKGROUND OF THE INVENTION

Various techniques are known for treating brain tissue.

In particular, a known technique developed by the Applicant consists in using a treatment apparatus comprising:
- an implantable intracranial device,
- a control unit remote from the intracranial device, and
- connection means between the intracranial device and the control unit.

The intracranial device is intended to be positioned in a burr hole made in a patient's skull. It comprises:
- a support,
- one (or more) transducer(s) for generating ultrasonic treatment waves, mounted on the support,
- one (or more) electric connection terminal(s) intended to cooperate with the connection means.

The control unit 2 is capable of supplying electrical energy to the intracranial device, and of adjusting its operating parameters.

The connection means are adapted to electrically connect the intracranial device to the control unit. They generally comprise:
- one (or more) electrical connection cable(s), one end of which is connected to the control unit, and
- one (or more) transdermal needle(s) connected to the other end of the cable.

The principle of operation of this device is as follows. Once the intracranial device is implanted in the patient's skull, a succession of treatment sessions is given to him to treat the pathology that affects him.

At each new treatment session, the intracranial device is connected to the control unit via connection means: the practitioner connects the cable to the control unit then inserts the needle through the patient's skin to the terminal of the ultrasonic device.

Once the end of the needle is connected to the terminal, the control unit can be activated to supply the ultrasonic device with electrical energy.

The technique described above allows effective treatment of brain conditions.

A purpose of the present invention is to propose an improved intracranial device allowing to increase the safety of the patient during the phase of connection of the intracranial device to the control unit, in particular during the insertion of the needle through the skin of the patient's skull.

Another purpose of the present invention is to propose an improved intracranial device whose risks of deterioration are reduced during the phase of connection of the intracranial device to the control unit, in particular during the insertion of the needle through the skin of the patient's skull.

BRIEF DESCRIPTION OF THE INVENTION

To this end, the invention proposes an implantable device at an aperture provided in the braincase of a patient, the implantable device comprising:
- a support plate including a first face and a second face opposite the first face,
- an ultrasonic unit intended to be mounted on the support plate, said ultrasonic unit comprising:
  - a housing including a bottom, at least one side wall and an upper face opposite the bottom, the housing being intended to be positioned on the first face of the support plate,
  - a plurality of transducers, disposed in the housing, for the generation of ultrasonic waves for treating a brain condition,
  - an electric connection terminal, attached to the housing, for connecting the ultrasonic unit to a remote control unit via electrical connection means, remarkable in that:
- the connection terminal comprises a pin projecting outwards from the housing in a direction perpendicular to the bottom and oriented from the bottom towards the upper face of the housing,
- the support plate comprises a through-opening for the pin to pass through,
- the implantable device further comprises an attachment piece including:
  - a conduit adapted to receive at least a portion of the pin, and
  - a peripheral collar extending perpendicularly to a longitudinal axis of the conduit,
- the collar being intended to contact the second face of the support plate to press the support plate against the housing when the ultrasonic unit, the support plate and the attachment piece are joined.

The fact that the ultrasonic unit, the support plate and the attachment piece consist of three independent components allows to facilitate the manufacture of the implantable device, each of these elements being able to be manufactured separately.

The fact that:
- the ultrasonic unit comprises a connection terminal projecting outwards, that
- the support plate comprises a through-opening for the connection terminal to pass through and that
- the attachment piece is intended to cooperate with the connection terminal once the latter has been inserted into the through-opening to press the support plate against the ultrasonic unit allows to facilitate the assembly of the various elements constituting the implantable device, and therefore the manufacturing method thereof.

The fact that the attachment piece comprises a collar allows:
- on the one hand, to protect the electronic board contained in the housing of the ultrasonic unit, in particular in the case where the practitioner would insert the transdermal needle at a position close to the blind hole intended to receive the needle, on the other hand, to limit the deformation of the support plate by distributing the force applied by the transdermal needle (when inserting it into the connection terminal) over a large surface of the support plate.

Preferred but non-limiting aspects of the present invention are as follows:

- the ratio between the width of the collar $L_{Coll}$ and the width of the conduit $L_{Cond}$ can be comprised between ¼ and 2, preferably ½ and ³⁄₂, and even more preferably equal to 1;
- the ratio between the width of the collar $L_{Coll}$ and the width of the upper face $L_{Log}$ of the housing can be comprised between ½ and 2, and preferably between ⅔ and 1;
- the collar can be circular in shape;
- the collar may comprise at least two diametrically opposite through-lumens;
- the pin may be cylindrical in shape and comprise a threading on its side wall, the conduit consisting of a nut the tapped hole of which is intended to cooperate by screwing with the threading of the side wall of the pin;
- the pin may comprise an upper wall opposite the bottom of the housing, and a blind hole intended to receive one end of the connection means, the upper wall including a countersink made at the entrance to the blind hole;
- the pin may comprise a stop at its base, the edge of the through-opening of the support plate being intended to bear against the stop when the pin is inserted into said through-opening;
- the edge of the through-opening of the support plate can be covered with a layer of polymeric material, such as silicone;
- the distance between the center of the through-opening and the barycenter of the plate can be non-zero.

The invention also relates to a system for imaging and/or treatment of a brain tissue, the system including a control unit and electrical connection means, remarkable in that the system further comprises an implantable device as described above.

BRIEF DESCRIPTION OF THE DRAWINGS

Other advantages and characteristics of the invention will emerge better from the following description of several variant embodiments, given by way of non-limiting examples, from the appended drawings in which.

DETAILED DESCRIPTION OF THE INVENTION

Figure 1:
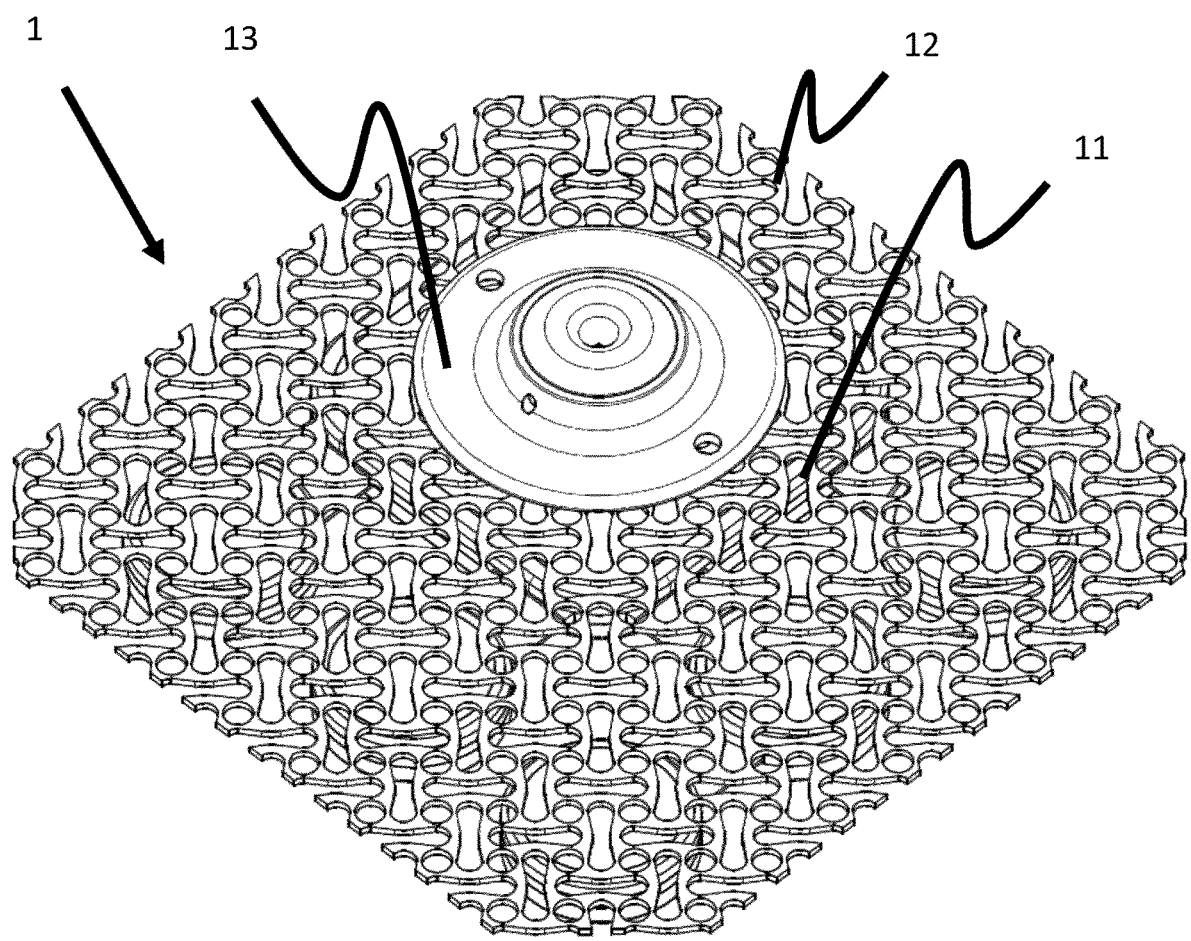
FIG. 1 is a schematic perspective representation of an implantable medical device.

An example of an implantable medical device will now be described with reference to the figures. In these various figures, the equivalent elements are designated by the same reference numeral.

1. Generalities

With reference to FIG. 1, the implantable medical device 1 comprises:
- an ultrasonic unit 11 for the emission of imaging or treatment ultrasonic waves,
- a support plate 12 on which the ultrasonic unit 11 is mounted, and
- an attachment piece 13 to block the ultrasonic unit 11 against the support plate 12.

Figure 2:
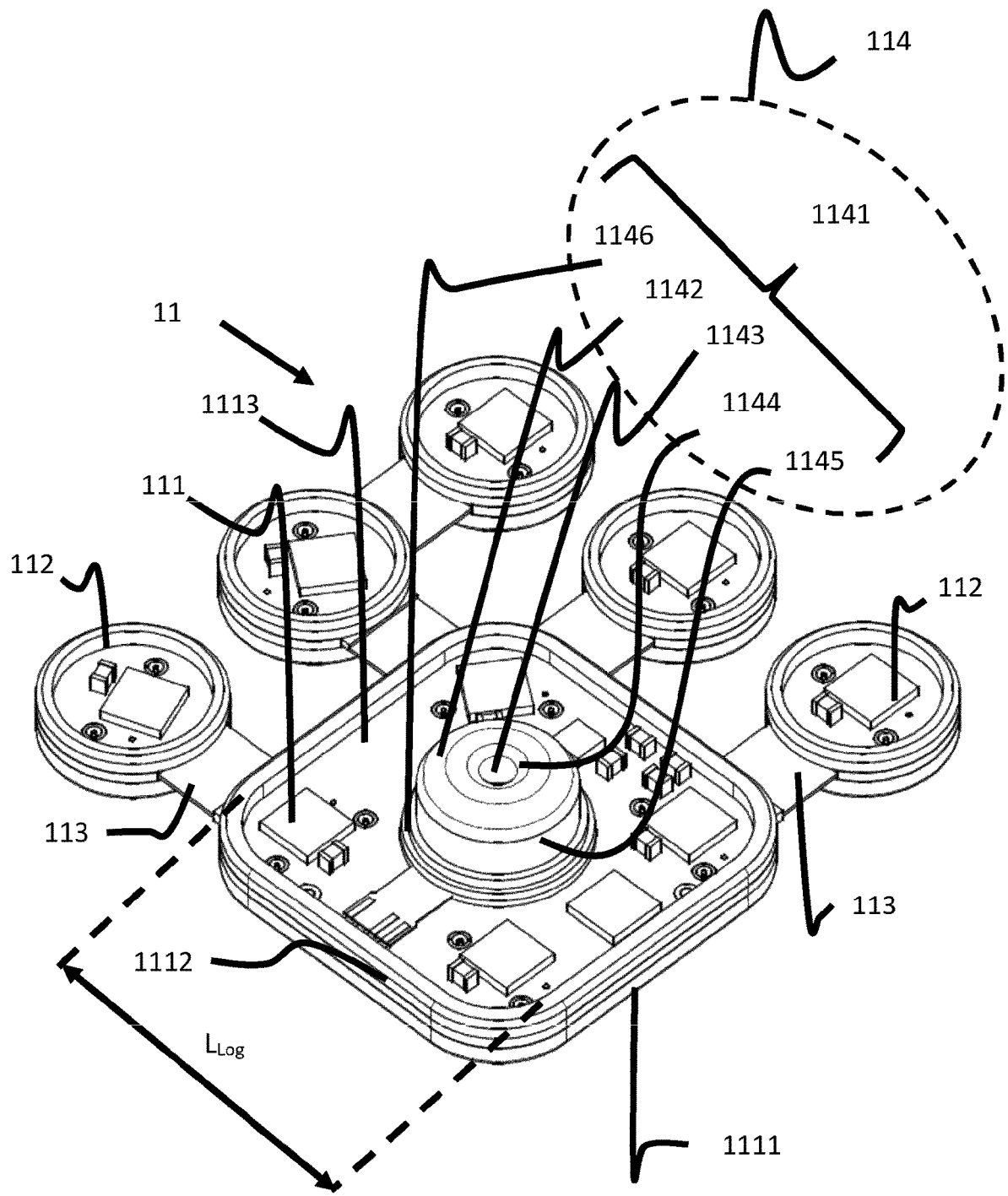
FIG. 2 is a schematic perspective representation of an ultrasonic unit of the implantable medical device.
Figure 3:
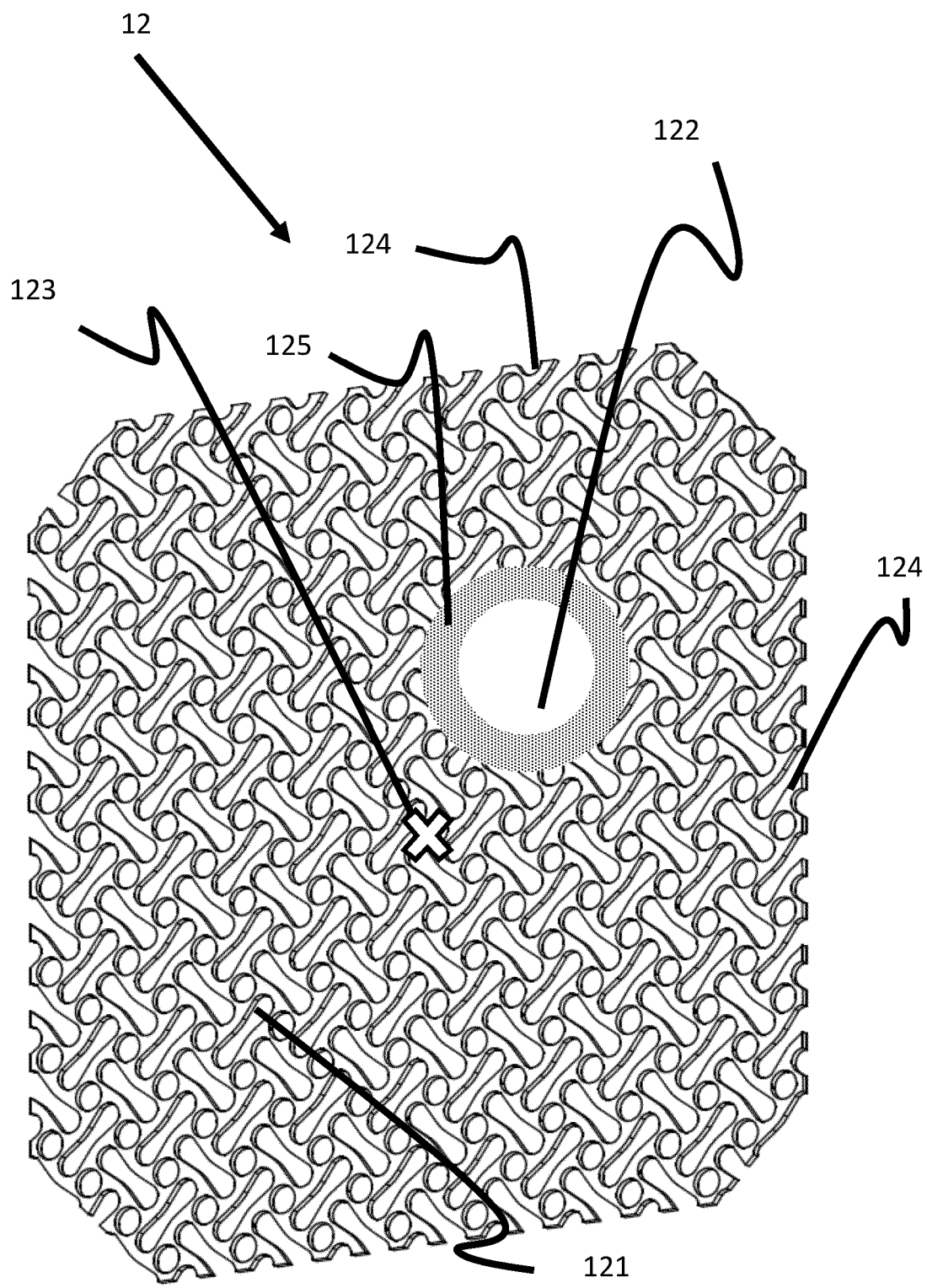
FIG. 3 is a schematic perspective representation of a support plate of the implantable medical device.
Figure 4:
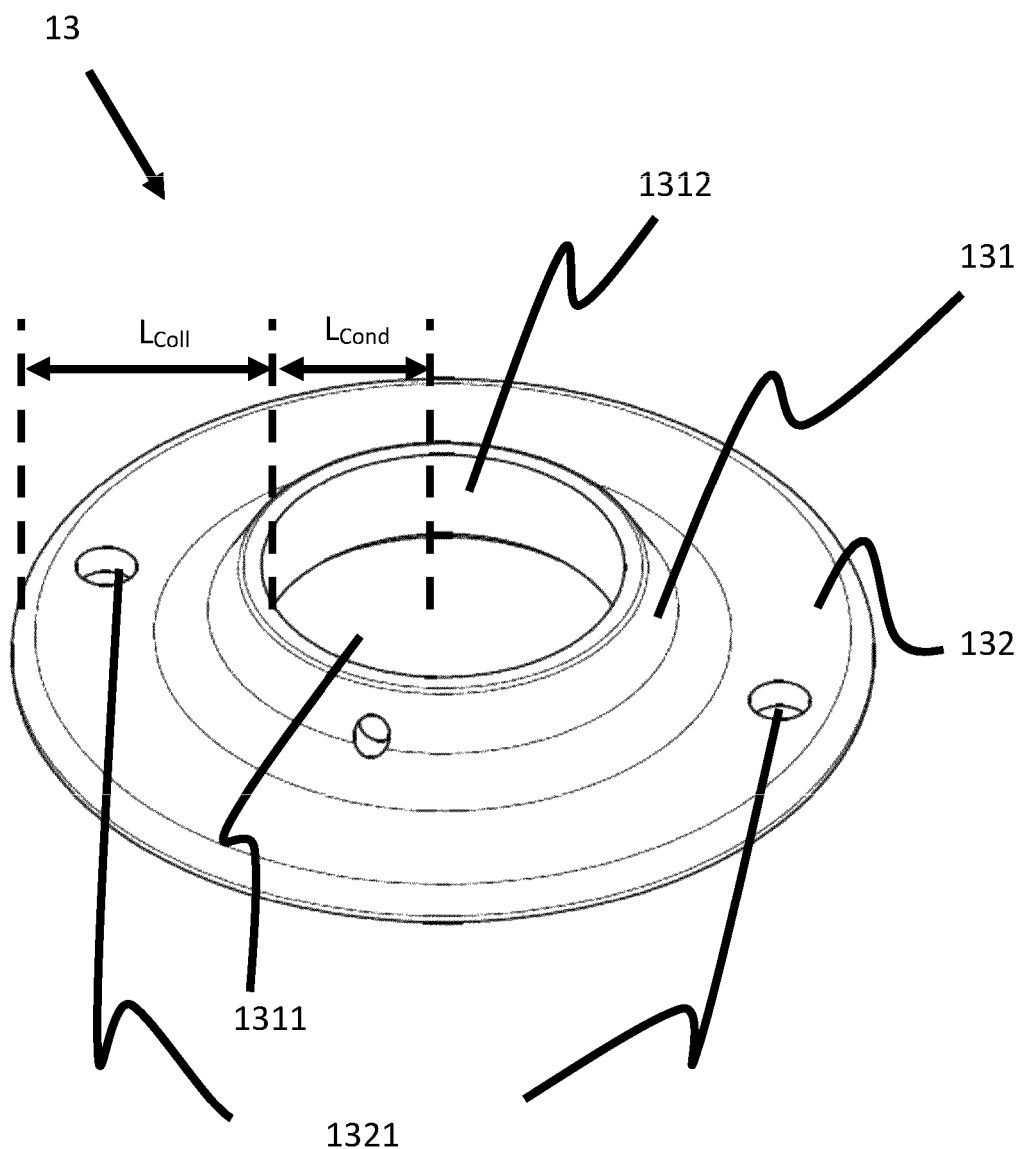
FIG. 4 is a schematic perspective representation of an attachment piece of the implantable medical device.

As shown in FIGS. 2 to 4, the ultrasonic unit 11, the support plate 12, and the attachment piece 13 are separate elements intended to be joined to form the implantable medical device 1. More specifically to form the implantable medical device 1, these different elements are joined so that the support plate 12 extends between the ultrasonic unit 11 and the attachment piece 13.

The medical device 1 is able to be implanted in a cranial bone of a patient to allow the treatment and/or imaging of a brain area of interest.

For this purpose, the practitioner performs a craniectomy. An incision is made in the scalp, then the skin (and muscles if present) is lifted (are lifted) to expose the skull. The skull is then cut to form a bone flap. The cranial bone flap is removed to make way for a cranial aperture in which the intracranial device can be positioned.

The positioning of the device 1 consists in inserting it into the cranial aperture so that the ultrasonic unit 11 extends facing the brain area of interest. Once the device 1 has been correctly positioned, the border 124 of the support plate 12 is attached to the periphery of the cranial aperture by any means known to the person skilled in the art (anchoring screws, gluing, etc.), then the scalp and the muscles are put back in place to cover the device 1. Thus, once implanted, the ultrasonic unit 11 faces the brain area of interest, while the attachment part 13 extends facing the scalp of the patient.

At each new treatment session, the practitioner electrically connects the medical device 1 to the remote control unit using the connection means. These connection means comprise in particular:
- an electrically conductive cable,
- a needle mounted at one end of the cable, the needle being capable of being inserted into a connection terminal of the ultrasonic unit, and
- a connection socket at the other end of the cable, the connection socket being able to be connected to a complementary socket of the control unit.

More specifically, the practitioner connects the connection socket to the remote control unit. The practitioner then inserts the needle into the patient's scalp, and introduces the end of the needle into a blind hole of the connection terminal so as to finalize the electrical connection of the ultrasonic device 1 to the remote control unit.

The different elements (ultrasonic unit, support plate, attachment piece) constituting the implantable medical device will now be described in greater detail.

2. Ultrasonic Unit

With reference to FIG. 2, the ultrasonic unit 11 comprises:
- a housing 111,
- an electric connection terminal 114 for connecting the ultrasonic unit 11 to a remote control unit.

2.1. Housing

The housing 111 includes a bottom 1111 and (one or) several side walls 1112. In the embodiment illustrated in FIG. 2, the upper face of the housing 111 opposite the bottom 1111 is open. In other words, the upper face of the housing has no upper wall. This promotes the dissipation to the outside of the heat generated by the electronic boards. Preferably, the upper face of the housing 111 is covered with parylene which has the advantage of being biocompatible.

This housing 111 is positioned on a first face of the support plate 12 when the medical device is assembled.

The housing 111 is designed to receive:
- a main electronic board 1113 adapted for exchanging electrical power and control signals with the remote control unit, and
- ultrasonic transducers—which are for example circular, 10 millimeters in diameter each—adapted to generate ultrasonic treatment (or imaging) waves of the brain area of interest.

Since the electronic board 1113 and the transducers are known to the person skilled in the art, the latter will not be described in more detail below.

The reader will nevertheless appreciate that in addition to the housing 111, the ultrasonic unit 11 can comprise secondary receptacles 112 each including a secondary electronic board and one (or more) additional transducer(s).

The housing 111 and the secondary receptacles 112 are distributed to form an array of regularly spaced transducers. The secondary electronic boards can be connected to the main electronic board 1113 via rigid—flex connectors 113 for the transfer of power supply and control signals from the external control unit (not shown). As illustrated in FIG. 1, the housing 111 and the receptacles 112 extend under the support plate 12, the dimensions of which are chosen so as to cover the ultrasonic unit 11, the support plate being intended to be attached on the patient's skull at its edges.

2.2. Connection Terminal

The electric connection terminal 114 is attached to the housing 111. It allows to connect the medical device 1 to the external control unit which supplies the transducers with electrical energy, and regulates their operating parameters.

As indicated above, the connection terminal is adapted to cooperate with the transdermal needle of the connection means.

More specifically, the connection terminal 114 comprises a pin 1141 projecting outwards from the housing 111 in a direction perpendicular to the bottom 1111 and oriented from the bottom 1111 towards the upper face of the housing 111.

The base of the pin preferably comprises a stop 1146 on which the support plate 12 is intended to bear. This allows to maintain a non-zero distance between the housing 111 of the ultrasonic unit 11 and the support plate 12 in order to limit contact between the housing 111 and the support plate 12. This allows to avoid damaging the parylene layer covering the housing 111 at its upper face.

The upper wall 1142 of the pin 1141 includes a blind hole 1143 into which the end of the needle of the connection means is intended to be introduced to electrically connect the ultrasonic unit 11 to the electrical connection means.

Advantageously, the connection terminal 114 may comprise a conical flare (or countersink) 1144 made at the entrance to the blind hole 1143. This facilitates the introduction of the end of the needle into the blind hole 1143. Indeed, as mentioned above, the connection terminal 114 is covered by the skin of the skull. It may therefore prove difficult for the practitioner to introduce the end of the needle into the blind hole 1143 during the electrical connection phase of the medical device 1 to the control unit. The presence of a countersink 1144 allows to facilitate this connection operation, the conical flare allowing the needle to be guided towards the blind hole 1143 when the end of the needle is close to the blind hole 1143.

As illustrated in FIG. 2, the side wall of the pin 1141 may comprise a threading 1145. This threading is intended to cooperate by screwing with a corresponding threading provided on the internal face of a conduit of the attachment piece. This allows to ensure the fixing of the ultrasonic unit 11, the support plate 12 and the attachment piece 13 during the assembly of the medical device 1. The fact that the ultrasonic unit 11 cooperates by screwing with the attachment piece 13 allows, during the connection phase of the intracranial device to the control unit, to distribute the force applied by the needle on the connection terminal to an entire surface of the support plate 12.

3. Support Plate

An example of support plate 12 is illustrated with reference to FIG. 3.

The support plate 12 is generally rectangular, but can have any shape, such as a circular, triangular or square shape. The dimensions of the support plate 12 (length and width) can be comprised between 1 and 15 centimeters.

The support plate 12 can be substantially planar. Alternatively, the support plate 12 can be curved or deformed to follow the curvature of the braincase of the patient.

In the embodiment illustrated in FIG. 3, the support plate 12 comprises a plurality of through-apertures 121. These through-apertures can be of different shapes (round, triangular, elliptical, pentagonal, hexagonal, honeycomb, diamond, etc.). The through apertures 121 can be obtained by drilling a solid plate, by chemical cutting, by molding, or by weaving wires—in particular metal wires—in order to form a mesh made up of mesh wires. The presence of through apertures in the support plate facilitates the deformation of the support plate in order to conform it to the shape of the patient's skull. In other embodiments, the support plate 12 can be a solid plate devoid of through apertures 121.

In all cases, the support plate 12 comprises a through-opening 122 for the pin to pass through the connection terminal. As illustrated in FIG. 3, the through-opening 122 is offset relative to the barycenter 123 of the support plate. More specifically, the through-opening 122 is formed in the support plate 12 so as to extend close to one (or more) of the borders 124 of the support plate 12. This allows to limit the risks of mechanical deformation of the support plate 12 when inserting the needle into the connection terminal to electrically connect the implantable medical device to the remote control unit.

The edge 125 of the through-opening 122 may be covered with a layer of polymeric material, such as silicone. In this case, the layer of polymer material is deposited on the edge 125 during assembly of the implantable medical device 1. This layer of polymer material allows to limit the risks of loosening between the connection terminal 114 and the attachment piece 13.

The material constituting the support plate 12 can be a metal, such as titanium or any other metal known to the person skilled in the art (optionally covered with parylene or the like if the metal used is not biocompatible per se). The use of a metal plate allows to limit its deformation in response to the application of a bearing force (for example mechanical deformation of less than 2.5 mm in response to a bearing force of 50 Newtons applied to the center of the plate). The use of titanium has many advantages, titanium being a very solid material and well accepted by the bone structure.

4. Attachment Piece

With reference to FIG. 4, the attachment piece 13 comprises:
- a conduit 131 capable of receiving the pin 1141, and
- a peripheral collar 132.

The conduit is intended to cooperate with the connection terminal so as to block the support plate between the ultrasonic unit and the attachment piece. More specifically, the conduit consists of a nut whose tapped hole is intended to cooperate by screwing with the threading 1145 of the side wall of the pin 1141. In other words, the internal face of the conduit 131 comprises a thread 1312 complementary to the threading 1145 of the side wall of the pin 1141.

The collar 132 extends at the base of the conduit 131, perpendicular to the axis of revolution of the conduit 131. It is intended to contact a second face of the support plate 12 opposite the first face facing the housing 111. The collar 132 allows the support plate 12 to be pressed against the stop 1146 when the ultrasonic unit 11, the support plate 12 and the attachment piece 13 are joined.

The ratio between the width $L_{Coll}$ of the collar 132 and the width $L_{Cond}$ of the conduit can be comprised between ¼ and 2, preferably ½ and ⅔, and even more preferably equal to 1. More specifically and with reference to FIG. 1, the dimensions of the collar 132 are chosen sufficient so that the assembly consisting of the surface covered by the conduit and the surface of the collar 132 covers almost entirely (that is to say at least ⅔ of) the upper face of the housing 111. In particular, the ratio between the width $L_{Coll}$ of the collar 132 and the width $L_{Log}$ of the upper face of the housing 111 (that is to say diameter in the case of an annular collar and/or of a upper face of a circular housing, diagonal between two opposite vertices in the case of a parallelepiped collar and/or an upper face of a parallelepiped housing, etc.) is comprised between ½ and 2, and preferably between ⅔ and 1. This allows to have a collar 132 with enough surface to protect the electronic board 1113 from possible damage caused by the end of the needle, in the event that the practitioner inserts it at a position offset from the blind hole 1143.

Preferably, the collar 132 is circular in shape. This allows a better distribution of the force applied by the needle during the introduction of the latter into the blind hole 1143 of the connection terminal 114.

Advantageously, the collar 132 can comprise two (or more than two) diametrically opposite through-lumens 1321. These lumens 1321 make it easier to screw the attachment piece 13 onto the pin 1141. These lumens also allow to apply, during manufacture, a predefined tightening torque to avoid any loss of sealing of the implantable device. Indeed, the pin 1141 is made in two parts (a first part mounted under the bottom of the housing and a second part mounted on the bottom, a seal (which must be compressed during assembly) being placed between the two parts).

The principle of assembly of the implantable device 1 is as follows. The operator inserts the pin 1141 of the connection terminal 114 through the through-opening 122 of the support plate 12. Once the ultrasonic unit 11 is in position on the first face of the support plate 12, the operator deposits the layer of polymer material (for example silicone) on the support plate, in particular at the edge 125 of the through-opening 122. The operator then disposes the attachment piece 13 on the connection terminal 114. The attachment piece 13 is installed on the pin 1141 so that the base of the conduit 131 (at which the collar 132 extends) is facing the second face of the support plate 12 (opposite the first face). The operator then screws the attachment piece 13 onto the pin 1141 using a tool (not shown) cooperating with the lumens 1321 made in the collar 131. The screwing of the attachment piece 13 causes the pressing of the collar 132 against the support plate 12 bearing against the stop 1146 of the connection terminal 114: the ultrasonic unit 11, the support plate 12 and the attachment piece are then integral. The implantable device 1 illustrated in FIG. 1 is thus obtained.

5. Conclusions

The implantable device 1 allows the treatment and/or imaging of a brain area of interest.

The presence of a collar 132 on the attachment piece 13 allows:
on the one hand, to protect the main electronic board 1113 against any damage that the needle could cause when inserting it under the skin of the patient's skull,
on the other hand, to limit the deformation of the support plate 12 by distributing the force applied by the end of the needle over a large surface of the support plate 12.

The reader will have understood that many modifications can be made to the invention described above without materially departing from the new teachings and advantages presented here.

For example, in the various embodiments described above, the support plate was made of a metal. It is obvious to the person skilled in the art that the support plate can be made of a material other than metal, such as for example:
a polymer material such as polyethylene, polystyrene, acrylic, polyetheretherketone (PEEK) or poly (methyl methacrylate) (PMMA),
a thermoplastic elastomer such as PEBAX.

Similarly, in the different embodiments described above, the ultrasonic unit 11, the support plate 12 and the attachment piece 13 were joined together by screwing the attachment piece 13 onto the pin 1141 of the ultrasonic unit 11. It is obvious that other attachment methods (gluing, force fitting, etc.) can be provided for joining the support plate 12 on the ultrasonic unit 11.

The invention claimed is:

1. An implantable device configured for positioning at an aperture provided in the braincase of a patient, the implantable device comprising:
a support plate including a first face and a second face opposite the first face,
an ultrasonic unit mounted on the support plate, said ultrasonic unit comprising:
a housing including a bottom, at least one side wall and an upper face opposite the bottom, wherein the upper face of the housing is positioned on the first face of the support plate,
a plurality of transducers, disposed in the housing, for the generation of ultrasonic waves for treating a brain condition,
an electric connection terminal, attached to the housing, for connecting the ultrasonic unit to a remote-control unit via electrical connection means including at least one needle, wherein:
the connection terminal comprises a pin projecting outwards from the housing in a direction perpendicular to the bottom and oriented from the bottom towards the upper face of the housing, wherein the pin includes a blind hole into which an end of the at least one needle is intended to be introduced to electrically connect the ultrasonic unit to the electrical connection means,
the support plate comprises a through-opening for the pin to pass through,
the implantable device further comprises an attachment piece including:
a conduit wherein at least a portion of the pin is received by the conduit, and
a peripheral collar extending perpendicularly to a longitudinal axis of the conduit, and wherein the peripheral collar contacts the second face of the support plate to press the support plate against the housing when the ultrasonic unit, the support plate and the attachment piece are joined.

2. The device according to claim 1, wherein the ratio between the width of the collar and the width of the conduit is comprised between ¼ and 2.

3. The device according to claim 1, wherein the ratio between the width of the collar and the width of the upper face of the housing is comprised between ½ and 2.

4. The device according to claim 1, wherein the collar is circular in shape.

5. The device according to claim 1, wherein the collar comprises at least two diametrically opposite through-lumens.

6. The device according to claim 1, wherein the pin is cylindrical in shape and comprises a threading on its side wall, the conduit consisting of a nut, wherein the tapped hole of the nut cooperates by screwing with the threading of the side wall of the pin.

7. The implantable device according to claim 1, wherein the pin comprises an upper wall opposite the bottom of the housing, and the blind hole which receives one end of the at least one needle of the electrical connection means, the upper wall including a countersink made at the entrance to the blind hole.

8. The implantable device according to claim 1, wherein the pin comprises a stop at its base, the edge of the through-opening of the support plate bears against the stop when the pin is inserted into said through-opening.

9. The implantable device according to claim 1, wherein the edge of the through-opening of the support plate is covered with a layer of polymeric material.

10. The implantable device according to claim 1, wherein the distance between the center of the through-opening and the barycenter of the plate is non-zero.

11. A system for imaging and/or treatment of a brain tissue, the system including a control unit and electrical connection means, wherein the system further comprises an implantable device configured for positioning at an aperture provided in the braincase of a patient, the implantable device comprising:

a support plate including a first face and a second face opposite the first face, an ultrasonic unit mounted on the support plate, said ultrasonic unit comprising:

a housing including a bottom, at least one side wall and an upper face opposite the bottom, wherein the upper face of the housing is positioned on the first face of the support plate, a plurality of transducers, disposed in the housing, for the generation of ultrasonic waves for treating a brain condition, an electric connection terminal, attached to the housing, for connecting the ultrasonic unit to the control unit via the electrical connection means, wherein the electrical connection means includes at least one needle, and wherein:

the connection terminal comprises a pin projecting outward from the housing in a direction perpendicular to the bottom and oriented from the bottom towards the upper face of the housing, wherein the pin includes a blind hole into which an end of the at least one needle is intended to be introduced to electrically connect the ultrasonic unit to the electrical connection means, the support plate comprises a through-opening for the pin to pass through, the implantable device further comprises an attachment piece including:

a conduit wherein at least a portion of the pin is received by the conduit, and a peripheral collar extending perpendicularly to a longitudinal axis of the conduit, and wherein the peripheral collar contacts the second face of the support plate to press the support plate against the housing when the ultrasonic unit, the support plate and the attachment piece are joined.

* * * * *